United States Patent [19]

Caizza

[11] Patent Number: 5,755,696
[45] Date of Patent: May 26, 1998

[54] SYRINGE FILLING AND DELIVERY DEVICE

[75] Inventor: Richard J. Caizza, Barry Lakes, N.J.

[73] Assignee: Becton, Dickinson and Company, Franklin Lakes, N.J.

[21] Appl. No.: 885,657

[22] Filed: Jun. 30, 1997

[51] Int. Cl.[6] .................................................. A61M 5/00
[52] U.S. Cl. ........................ 604/164; 604/263; 604/411
[58] Field of Search .................................. 604/164, 165, 604/169, 170, 192, 198, 263, 411

[56] References Cited

U.S. PATENT DOCUMENTS

| | | | |
|---|---|---|---|
| 2,389,355 | 11/1945 | Goland et al. | 128/214 |
| 3,662,754 | 5/1972 | Halloran | 128/221 |
| 4,139,009 | 2/1979 | Alvarez | 128/218 |
| 4,846,804 | 7/1989 | Davis et al. | 604/164 |
| 4,846,809 | 7/1989 | Sims | 604/198 |
| 4,850,996 | 7/1989 | Cree | 604/198 |
| 4,906,236 | 3/1990 | Alberts et al. | 604/198 |
| 4,998,922 | 3/1991 | Kuracina et al. | 604/192 |
| 5,360,408 | 11/1994 | Vaillancourt | 604/198 |
| 5,407,431 | 4/1995 | Botich et al. | 604/164 X |
| 5,411,499 | 5/1995 | Dudar et al. | 604/411 |
| 5,425,718 | 6/1995 | Tay et al. | 604/165 |
| 5,472,430 | 12/1995 | Vaillancourt et al. | 604/198 |
| 5,540,662 | 7/1996 | Nicholson | 604/110 |
| 5,549,558 | 8/1996 | Martin | 604/110 |
| 5,562,634 | 10/1996 | Flumene et al. | 604/164 X |
| 5,573,510 | 11/1996 | Isaacson | 604/164 X |
| 5,584,819 | 12/1996 | Kopfer | 604/239 |
| 5,609,584 | 3/1997 | Gettig et al. | 604/283 |

*Primary Examiner*—John D. Yasko
*Attorney, Agent, or Firm*—John L. Voellmicke

[57] ABSTRACT

A fluid transfer device comprises an access cannula assembly including a cannula having a proximal end, a distal end and a lumen therethrough, a cutting edge at the distal end of the cannula for piercing a vial stopper and a hub having an open proximal end and a distal end joined to the proximal end of the cannula so that the lumen is in fluid communication with the proximal end of the hub. A blunt cannula assembly includes a blunt cannula having a proximal end, a distal end, and a passageway therethrough, and a housing having an open proximal end and a distal end joined to the proximal end of the cannula. A spring is provided for helping to position the access cannula within the passageway of the blunt cannula wherein a proximally directed force applied to the blunt cannula will cause the spring to deflect and the cutting edge of the access cannula to project distally outwardly past the distal end of the blunt cannula.

20 Claims, 7 Drawing Sheets

SYRINGE FILLING AND DELIVERY DEVICE

FIELD OF THE INVENTION

The subject invention relates to a device mountable on a hypodermic syringe or other fluid delivery device which enables access to medication or other injectable liquid in vials having elastomeric closures and the subsequent delivery of the medication or injectable liquid.

BACKGROUND

A typical hypodermic syringe includes a syringe barrel with a mounting collar for threadedly engaging the hub of a needle assembly. The needle assembly includes a hub and a needle cannula which are connected. In cases where the needle assembly is maintained separately from the syringe until shortly prior to use, the medical practitioner selects an appropriate needle assembly for the procedure being carried out. The needle assembly is removed from its sterile package, and the hub of the needle assembly is threadedly engaged with the mounting collar of the syringe barrel.

Liquid pharmaceuticals and other injectable liquids are often stored in rigid containers which can be accessed using a hypodermic syringe. Some containers for liquid pharmaceuticals are glass vials with an elastomeric closure that can be penetrated by the needle of a hypodermic syringe. To access the liquid in a vial, the plunger of the hypodermic syringe is moved in a proximal direction to draw into the syringe barrel a volume of air substantially equal to the volume of medication that is desired. The sharp distal end of the needle is then urged through the elastomeric closure of the vial, and the air in the syringe barrel is injected into the vial. The distal end of the needle and the vial engaged therewith are then pointed gravitationally upwardly. The practitioner ensures that the distal tip of the needle is covered by the medication in the vial by manipulating the needle and the vial with respect to each other. The plunger of the hypodermic syringe is then moved proximally to draw the desired volume of medication through the needle and into the chamber of the syringe barrel.

After withdrawing a desired volume of medication from a vial, the medical practitioner may inject the medication into either a patient, another vial or an injection site of an intravenous set or catheter. There is a trend toward needleless I.V. systems which do not require a pointed needle cannula to pierce the injection site of an I.V. set. There are systems that have injection sites covered by a pre-slit septum which can be accessed by a blunt cannula. Accordingly, after withdrawing medication from a vial using a sharp needle the user must remove the needle and install a blunt cannula if the medication will be used with an I.V. set having a pre-slit septum. The user must take care to avoid accidental needle stick using a needle to draw medication into a syringe and in the act of removing the needle to replace it with a blunt cannula. Also, there is the potential of contaminating the components when they are installed and removed during the filling and delivery process.

Also, at the time of prefilling the syringe it may not be known whether medication will be injected through an injection site having a pre-slit septum, which requires a blunt cannula, or through an injection site having a pierceable elastomeric septum which requires a needle assembly having a cannula sharp enough to pierce the septum. In this latter case the practitioner may use the hypodermic needle assembly which was used to fill the syringe.

Accordingly, there is a need for a device which will allow filling of a syringe from a vial having a pierceable stopper and the subsequent delivery of the medication to an I.V. set through a blunt cannula without having to handle or reshield sharp needles. There is also a needle for a single device which can be used for withdrawing medication from a vial having a pierceable stopper and for injecting this medication through an injection site having a pierceable septum or a pre-slit septum without the need of changing components during the procedure.

SUMMARY OF THE INVENTION

The subject invention relates to a fluid transfer device comprising an access cannula assembly including an access cannula having a proximal end, a distal end, and a lumen therethrough. A cutting edge at the distal end of the access cannula is provided for piercing a vial stopper or a pierceable septum of an injection site. A hub has an open proximal end and a distal end joined to the proximal end of the access cannula so that the lumen is in fluid communication with the open proximal end of the hub. A blunt cannula assembly includes a blunt cannula having a proximal end, a blunt distal end, and a passageway therethrough, and a housing having an open proximal end and a distal end joined to the proximal end of the blunt cannula. A portion of the access cannula is positioned within the passageway of the blunt cannula. A spring is provided for helping to position the access cannula within the passageway of the blunt cannula wherein a proximally directed force applied to the blunt cannula will cause the spring to deflect and the cutting edge of the access cannula to project distally outwardly past the distal end of the blunt cannula. Sealing structure is provided for sealing the access cannula assembly and the blunt cannula assembly so that pressurized liquid passing through the access cannula will exit the fluid transfer device through the distal end of the blunt cannula.

A method for transferring an injectable liquid comprising the steps of:

(a) providing a syringe including a syringe barrel having an elongate cylindrical body defining a chamber for retaining fluid, an open proximal end, a distal end and a tip extending from said distal end having a tip passageway therethrough in fluid communication with the chamber, a stopper in fluid-tight slidable engagement inside the barrel and an elongate plunger rod extending proximally from the stopper through the open proximal end of the barrel;

(b) providing a fluid transfer device comprising an access cannula assembly including an access cannula having a proximal end, a distal end, and a lumen therethrough, a cutting edge at the distal end of the access cannula for piercing a vial stopper, a hub having an open proximal end and a distal end joined to the proximal end of the access cannula so that the lumen is in fluid communication with the open proximal end of the hub; a blunt cannula assembly including a blunt cannula having a proximal end, a blunt distal end, and a passageway therethrough, a housing having an open proximal end and a distal end joined to the proximal end of the blunt cannula; spring means for helping to position the access cannula within the passageway of the blunt cannula wherein a proximally directed axial force applied to the blunt cannula will cause the spring to deflect and the cutting edge of the access cannula to project distally outwardly past the distal end of the blunt cannula; and means for sealing the access cannula assembly and the blunt cannula assembly so that pressurized liquid passing distally through the access cannula will exit the fluid transfer device through the distal end of the blunt cannula;

(c) connecting the syringe filling device to the syringe so that the tip is positioned within the open proximal end of the hub, and the chamber is in fluid communication with the lumen of the access cannula;

(d) providing a vial having a pierceable stopper and containing an injectable liquid;

(e) placing the blunt distal end of the blunt cannula in contact with the pierceable stopper;

(f) moving the syringe barrel toward the septum causing the spring to deflect and move the blunt cannula assembly proximally and causing the cutting edge on the distal end of the access cannula to pierce the pierceable stopper to establish fluid communication between the interior of the vial and the chamber of the syringe;

(g) withdrawing the desired amount of injectable liquid from the vial into the chamber by moving the plunger rod in a proximal direction with respect to the barrel; and (h) withdrawing the access cannula from the stopper of the vial.

DETAILED DESCRIPTION

While this invention is satisfied by embodiments in many different forms, there are shown in the drawings and will be herein described in detail a preferred embodiment of the invention with the understanding that the present disclosure is to be considered exemplary of the principals of the invention and not intended to limit the scope of the invention to the embodiment illustrated. The scope of the invention will be measured by the appended claims and their equivalents.

Referring to FIGS. 1–8, a fluid transfer device 20 of the present invention includes an access cannula assembly 21 including an access cannula 22 having a proximal end 23, a distal end 25, and a lumen therethrough. A cutting edge 28 is provided at the distal end of the access cannula for piercing a vial stopper or a pierceable septum of an I.V. set injection site. A hub 29 having an open proximal end 31 and a distal end 32 which is joined to the proximal end of the access cannula so that the lumen of the access cannula is in fluid communication with the open proximal end of the hub.

A blunt cannula assembly 33 includes a blunt cannula 34 having an open proximal end 35, a blunt distal end 37, and a passageway 38 therethrough. A housing includes an open proximal end 41 and a distal end 43 joined to the proximal end of the blunt cannula. Although the blunt cannula assembly can be made by joining a separate housing and blunt cannula in this embodiment is preferably integrally formed of thermoplastic material having a one-piece construction. The vial access cannula assembly and the blunt cannula assembly are positioned in a concentric relationship wherein a portion of access cannula 22 is within the passageway 38 of the blunt cannula.

Figure 6:
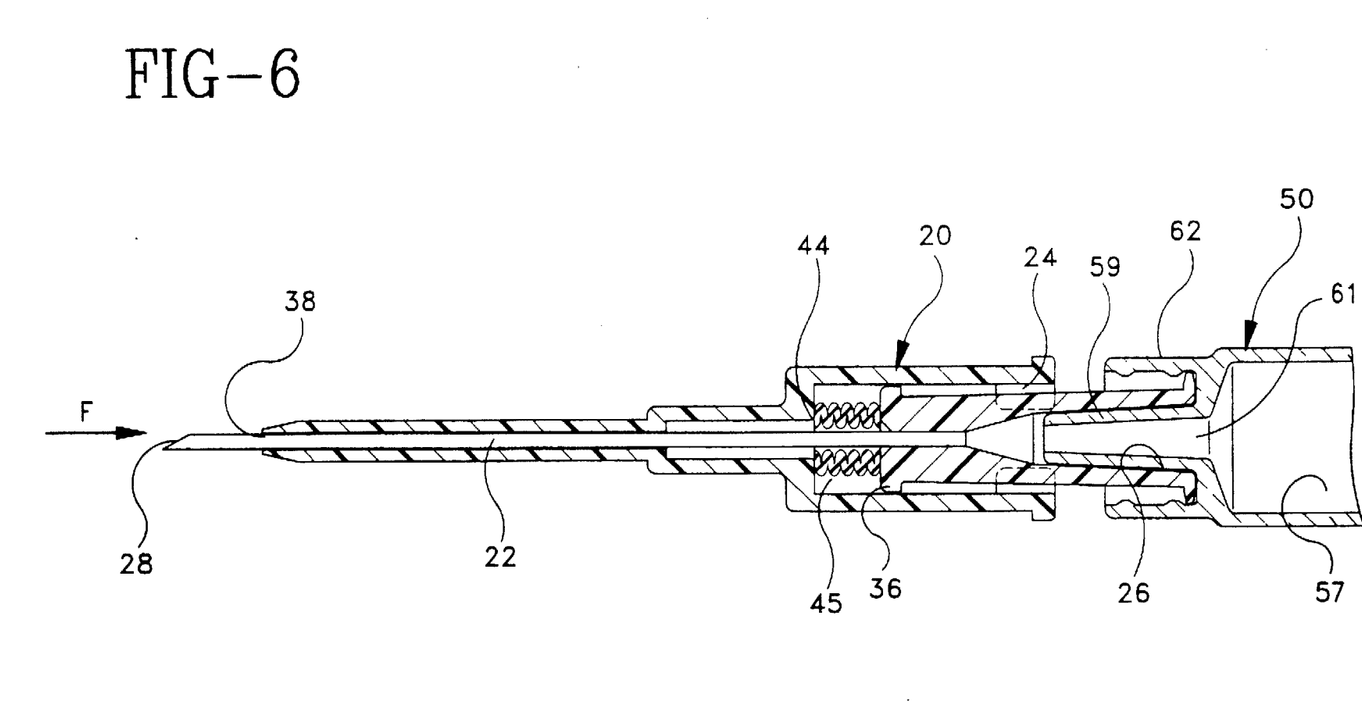
FIG. 6 is a fluid transfer device of FIG. 5 further illustrating the cutting edge of the access cannula protruding from the distal end of the blunt cannula.

A spring 45 is positioned between hub 29 and housing 40 for helping to position access cannula 22 within passageway 38 of blunt cannula 34 wherein a proximally directed axial force F, as illustrated in FIG. 6, applied to the blunt cannula will cause spring 45 to deflect and cutting edge 28 of access cannula 22 to project distally outwardly past blunt distal end 37 of the blunt cannula. Spring 45 in this embodiment is preferably made of elastic material such as natural rubber, synthetic rubber or thermoplastic elastomer. Spring 45 includes a longitudinal conduit 46 which allows it to be slidably placed over access cannula 22 and trapped between hub 29 and housing 40. The spring may also be a coil spring similarly placed or placed elsewhere such as adjacent to the access cannula rather than around the access cannula. The spring can also be constructed of cantilever elements projecting to or from the housing or the hub so that the cantilever elements are deflected upon axial movement of the housing toward the hub. The spring element may also be placed around the periphery of the hub, for example, between projections 30 on the hub and the proximal end of the housing.

The fluid transfer device of the present invention also preferably includes means for sealing the access cannula assembly and the blunt cannula assembly so that pressurized liquid passing distally through the access cannula will exit said fluid transfer device through the distal end of the blunt cannula. The means for sealing helps assure that liquid intended for delivery from the blunt distal end of the blunt cannula does not exit the fluid transfer device in other areas. For example, moving through the space between the outside surface of the access cannula and the passageway of the blunt cannula to escape through the space between the hub and the housing. Means for sealing can be accomplished by making the access cannula large enough to substantially occlude the passageway of the blunt cannula to help prevent liquid from passing between the outside of the cannula and the inside of the passageway. Sealing means can also be accomplished by placing a resilient sealing element such as an O-ring or molded annular flange which can seal the space between the access cannula assembly and the blunt cannula assembly. In this preferred embodiment, spring 45 also functions as a sealing means. In particular, spring 45 is an elastomeric cylindrically shaped element which fits around cannula 22 and is slightly compressed when the fluid transfer device is in its resting position so that distal end 47 of the spring seals the periphery of cannula 22 and annular edge 44 in the housing to resist the passage of liquid in a proximal direction from the space between the outside of the access cannula and the passageway of the blunt cannula. The elastomeric element can preferably seal the space between the cannula and the housing or between the hub and the housing or both.

In this embodiment the access cannula assembly preferably includes access cannula 22 being formed of metal such as stainless steel and hub 29 being formed of a thermoplastic material with the components being joined together by various means including epoxy adhesive. The use of a metal cannula allows a small outside diameter while still maintaining considerable strength. Also, the dimensions and tolerances of the outside diameter of the metal cannula can be closely held for slidable engagement within passageway 38 of the blunt cannula to help function as sealing means as described hereinabove. Also, the high strength and reduced diameter of a metal cannula helps reduce penetration forces as the cannula enters a vial stopper or pierceable septum. It is also within the purview of the instant invention to have an access cannula assembly wherein the cannula and the hub are integrally formed of a single material such as thermoplastic.

The fluid transfer device of the present invention is suitable for use with fluid delivery devices such as syringes. For the purpose of illustration, fluid transfer device 20 is connected to a syringe 50 comprising a syringe barrel 51 having a distal end 52, an open proximal end 53 and a circular side wall 55 defining a chamber 57 for retaining fluid. Volume measuring indicia 58 are on the barrel for measuring the volume of liquid to be delivered. The distal end of the syringe barrel is connected to hub 29 so that the lumen of access cannula 22 is in fluid communication with chamber 57 of the syringe barrel. In this embodiment, distal end 52 of the syringe barrel includes a frusto-conically shaped tip 59 which engages at frusto-conically shaped surface 26 in open proximal end 31 of the hub. The distal end of the syringe barrel also preferably, but not necessarily, includes a locking luer-type collar 62 concentrically surrounding tip 59. The luer collar has an internal thread 63 which engages radial projections 30 on hub 29 to hold the hub securely to the barrel. It is within the scope of the present invention to include various hub configurations to attach to a variety of other medical fluid handling devices. The hub configuration described hereinabove, having a frusto-conically shaped interior cavity, reflects one of these many possibilities. Many syringes and fluid handling devices, such as stopcocks and adapters, and other fluid handling devices contain luer slip and locking luer-type fittings to which a hub having a frusto-conically shaped interior cavity will properly engage. It is within the purview of the present invention to provide a fluid transfer device wherein the hub of the access cannula assembly is integrally molded with the syringe barrel.

A stopper 64 is positioned in chamber 57 in sliding fluid-tight engagement with circular side wall 55. A rigid elongate plunger rod 65 is connected to the stopper and extends proximally through the open proximal end of barrel 51. The stopper and the plunger rod can be made of one-piece unitary construction. Force applied to the plunger rod causing sliding movement of the stopper in a proximal direction draws fluid through conduit 61 into chamber 57. Conversely, sliding movement of stopper 64 in a distal direction urges fluid from chamber 57 through conduit 61.

Fluid transfer device 20 preferably, but not necessary, includes a removable shield 67 having an open proximal end 68, a distal end 69 and a side wall 70 therebetween defining a recess 71 in the shield. The shield is removably connected to the fluid transfer device so that blunt cannula 34 is contained within recess 71 of the shield. The shield helps protect the blunt cannula from contamination before use. In this embodiment the shield preferably frictionally engages housing 40 of the blunt cannula assembly. However, it is within the purview of the present invention to provide a shield which engages the hub of the access cannula.

Figure 1:
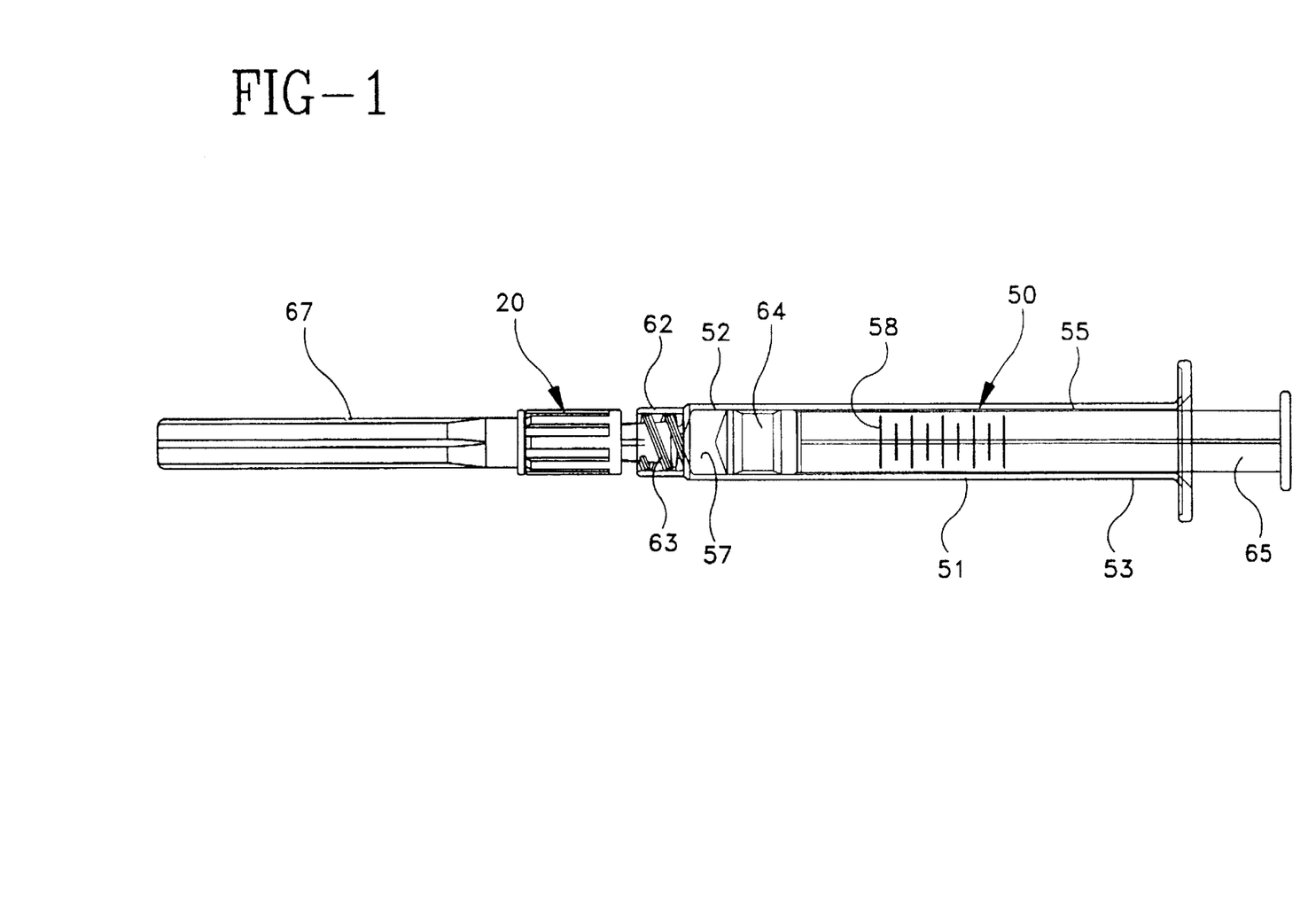
FIG. 1 is a side-elevational view of the fluid transfer device of the present invention attached to a syringe.
Figure 2:
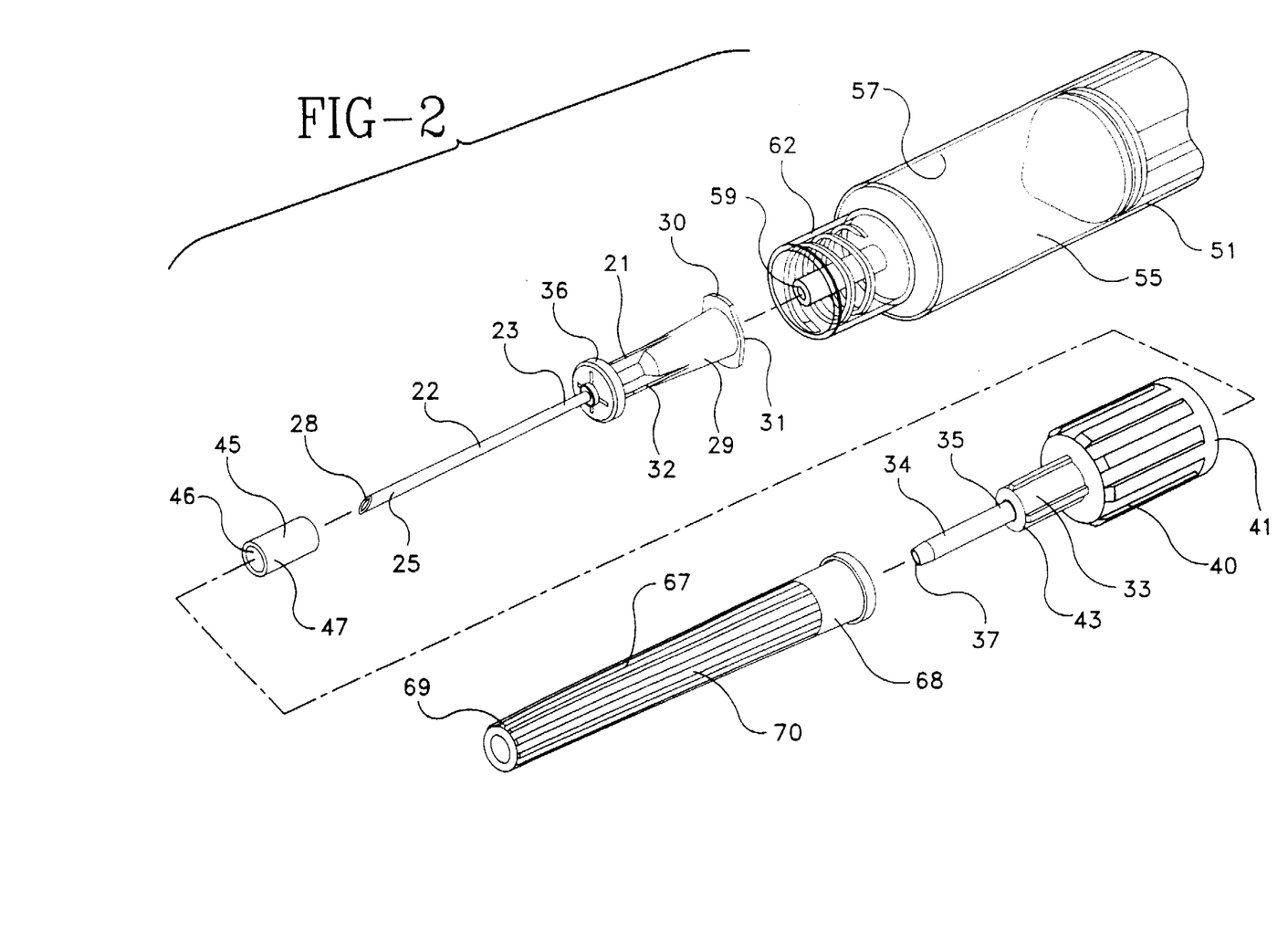
FIG. 2 is an exploded view of the fluid transfer device of the present invention and a syringe barrel.
Figure 3:
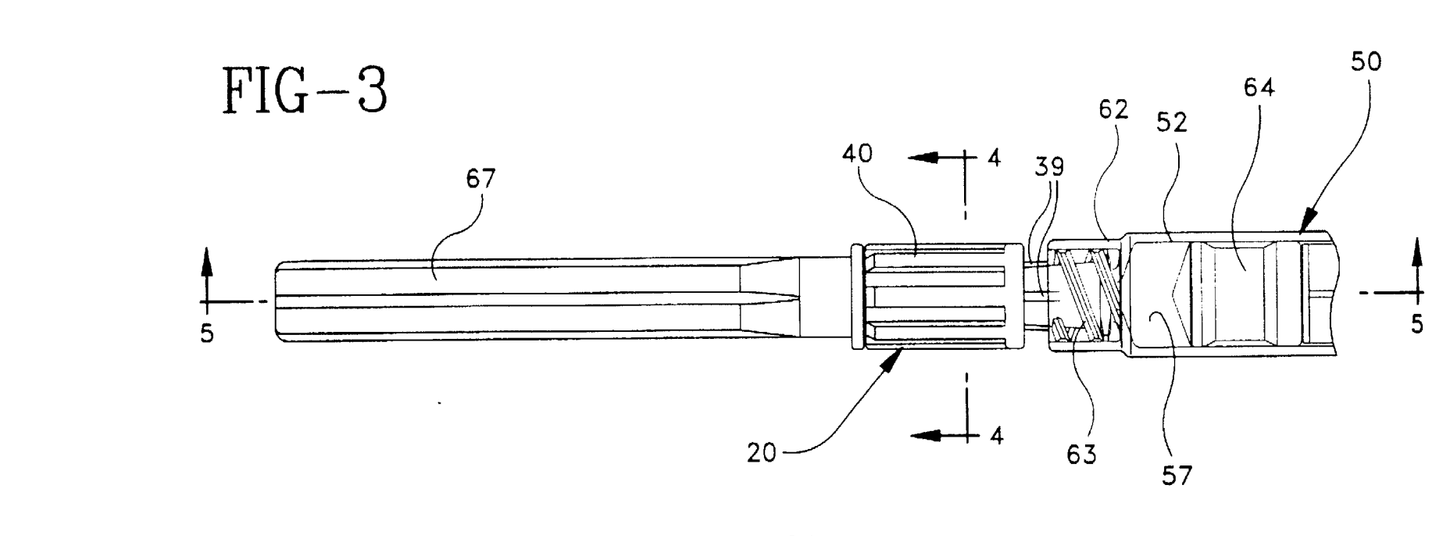
FIG. 3 is an enlarged side-elevation view of the fluid transfer device.
Figure 4:
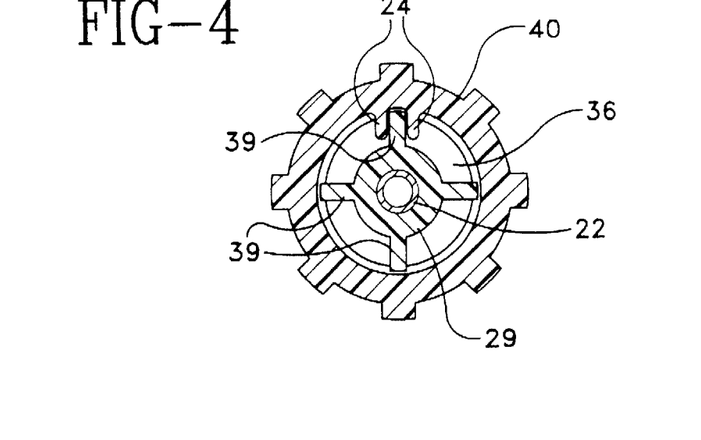
FIG. 4 is a cross-sectional view of the fluid transfer device of FIG. 3 taken along line 4—4.
Figure 5:
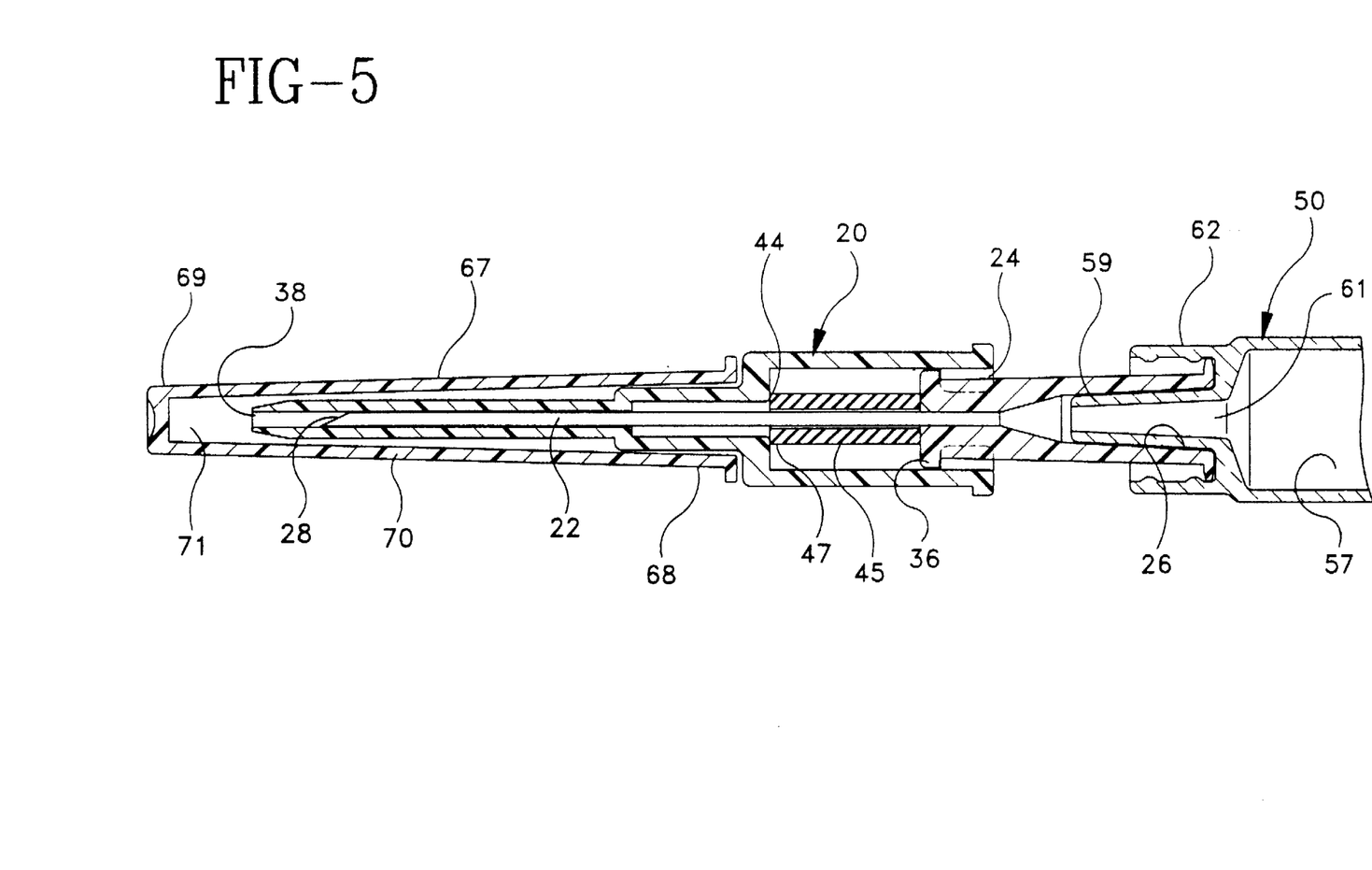
FIG. 5 is a cross-sectional view of the fluid transfer device of FIG. 3 taken along line 5—5.

When connecting fluid transfer device 20 to a syringe such as syringe 50 having a locking luer-type collar the fluid transfer device is rotated to advance projections 30 on hub 29 along internal thread 63 of collar 62. The rotation will pull the hub toward the syringe barrel tightly engaging tip 59 of the syringe barrel into the open proximal end of hub 29. Because of the torque required to engage the fluid transfer device and a syringe barrel having a locking luer-type collar it is desirable to have torque transmitting means for allowing rotational force applied to the housing of the blunt cannula to be transmitted to the hub of the access cannula assembly so that the user has a larger surface to manually apply rotational forces to the fluid transfer device and such forces are effectively transmitted to the hub. In this embodiment torque transmitting means includes one or more protuberances on the hub such as axial ribs 39 which engage a slot in housing 40 formed by axial projections 24 as best illustrated in FIG. 4. Any combination of protuberances and/or recesses on the hub or housing which are capable of transmitting sufficient torque to engage the hub to the syringe barrel are satisfactory for functioning as torque transmitting means.

It is also preferred to have structure for connecting the hub and the housing to prevent the blunt cannula assembly from being separated from the access cannula assembly and with certain spring configurations, to keep the spring under a slight compressive force, especially when the spring is also being used as sealing means. In this embodiment, barrier wall 36 at the distal end of hub 29 engages longitudinal ribs 24 to help prevent separation of the blunt cannula assembly and the access cannula assembly. These components must be configured to allow the longitudinal ribs to snap over the barrier wall during assembly of the fluid transfer device.

Fluid transfer device 20 of the present invention, coupled with a fluid delivery device, such as syringe 50 can be used to access fluid in a vial having a pierceable stopper and deliver the fluid to an injection site on an I.V. set or catheter regardless of whether the injection site has a pre-slit septum or a pierceable septum. This is a major advantage of the present invention. No longer are multiple devices needed to fill a syringe from a stoppered vial and deliver the liquid or other medication through an I.V. injection site having a pre-slit septum. The instant invention contains a blunt cannula and an access cannula having a cutting edge at its distal end which is sharp enough to pierce rubber stoppers and septums but does not have to be and is preferably not sharp enough for injection through the skin. Accordingly, there will be less chance to pierce the skin with a dull cutting edge suitable for vial stopper piercing but not for skin injection.

Figure 7:
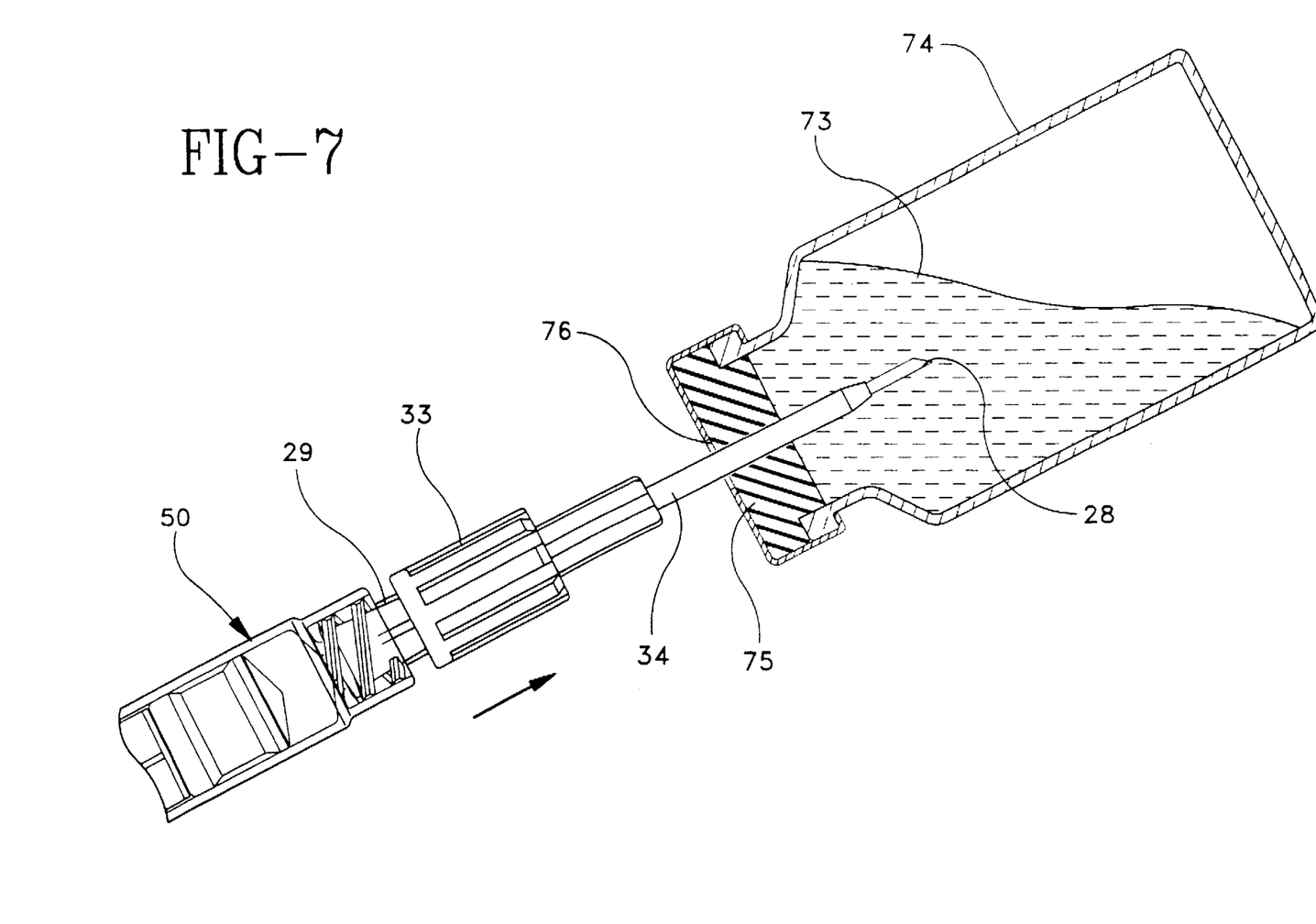
FIG. 7 is a side-elevational view of the fluid transfer device and syringe being used to draw liquid from a stoppered vial.

As best illustrated in FIG. 7 the fluid transfer device can be used with syringe 50 to access injectable liquid or medication, such as fluid 73, contained within vial 74 having a pierceable stopper 75. The fluid is accessed by placing the blunt distal end of the blunt cannula on top surface 76 of stopper 75 and applying an axial force through the syringe barrel in direction A. Because the blunt cannula cannot pierce the vial stopper, the top surface of the vial stopper responding with an equal and opposite force to force A, will push the blunt cannula assembly axially proximally toward hub 29 causing the spring to compress and cutting edge 28 of the access cannula to protrude outwardly from the distal end of the blunt cannula and pierce the stopper 75. When force A is discontinued the cutting edge will, by action of the spring, retract back into the passageway of the blunt cannula. At this point, liquid can be drawn into the syringe barrel using known methods such as the method described hereinabove. The fluid transfer device is then withdrawn from the stopper of the vial.

Figure 8:
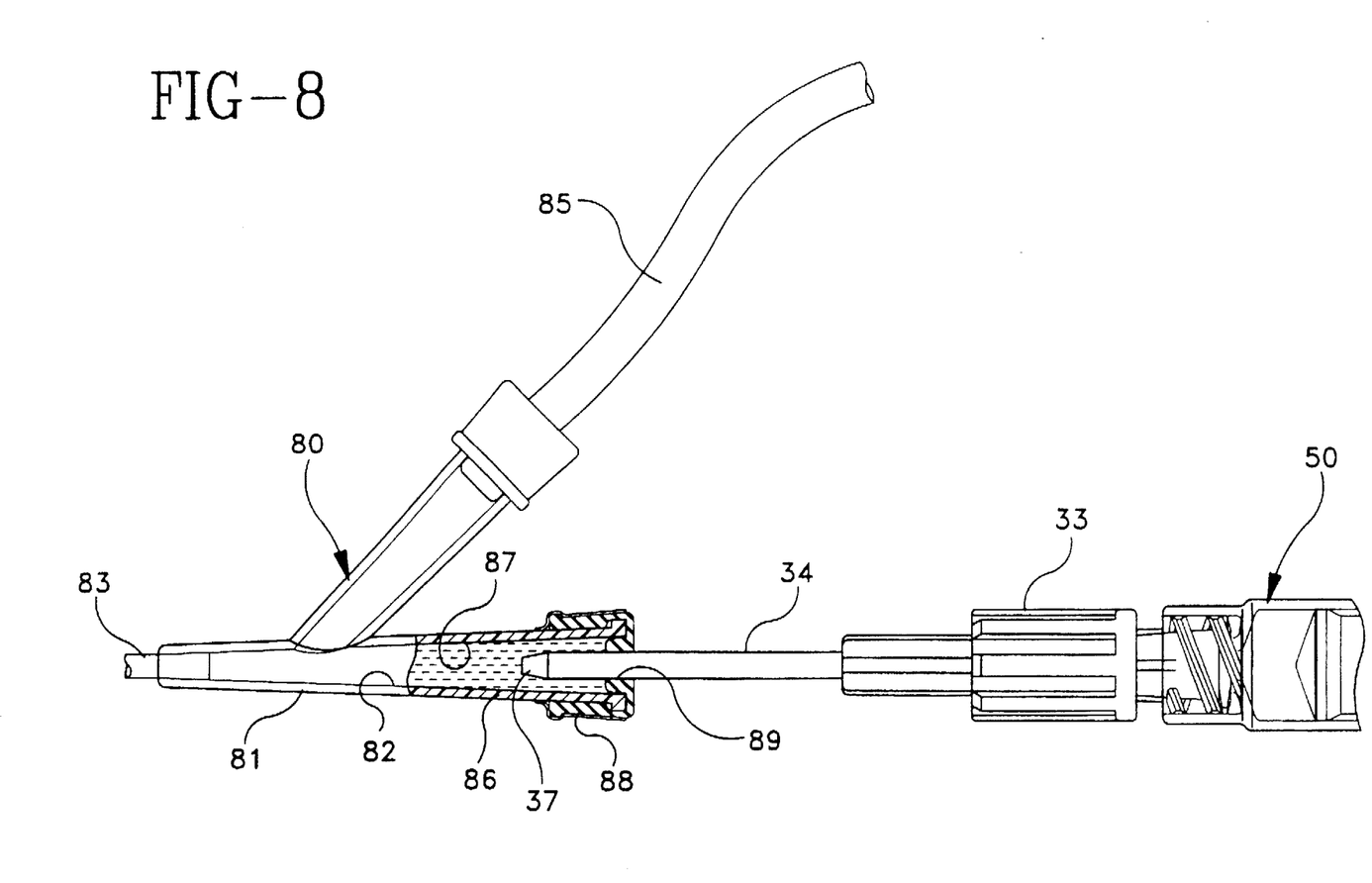
FIG. 8 is a side-elevational view illustrating the fluid transfer device and syringe being used to inject liquid into an injection site of an I.V. set.

The filled syringe 50 with fluid access device 20 attached is now transferred to the point of use where it can be used to inject fluid into a patient through an I.V. set or a catheter having an injection site with a pre-slit or pierceable septum. Specifically, as illustrated in FIG. 8, an I.V. set 80 can include a a housing 81 having a hollow interior conduit 82 and a flexible tube 83 connected to the vascular system of a patient, usually through a catheter. Housing 81 also includes another flexible tube 85 which is connected to a source of I.V. fluid. Housing 81 also includes port 86 having a conduit 87 therethrough in communication with the interior conduit 82. A pre-slit septum 88 covers the open end of conduit 87. The most common ports are covered by pierceable septums or pre-slit septums and are known in the art and sometimes referred to as "PRN" from the Latin pro re nata meaning "as the need arises". Septum 88 is a pre-slit septum having a slit 89 therein. Septum 88 effectively seals conduit 87 from the exterior of the housing. However, access to the conduit can be achieved by pressing blunt distal end 37 of blunt cannula 34 against the area of the septum containing slit 89. General force applied to the syringe in an axial direction will cause the blunt end of the cannula to enter the conduit through the slit which is forced open by the blunt cannula. Preferably, the force required to open the slit is less than the force required to compress the spring and allow the cutting edge of the access cannula to protrude from the distal end of the blunt cannula. The liquid may now be injected into the I.V. set. Upon completion and removal of the blunt cannula from the conduit, the slit portion of the septum automatically reseals itself. If the septum on the port of the I.V. set is not pre-slit. The fluid access device of the present invention can be used in the same manner as it is used with a pre-slit septum. However, the greater force required to penetrate a pierceable, non-pre-slit septum will cause the spring to compress and the cutting edge of the access cannula to protrude beyond the distal end of the blunt cannula to pierce the septum in a similar manner as when the fluid transfer device is used to pierce the pierceable stopper of the medication vial. The fluid access device of the present invention effectively seals itself so that fluid may be injected through the access cannula or through the blunt cannula, and the cutting edge of the access cannula may be exposed solely by axial proximally directed force exerted on the distal end of the blunt cannula. When the axial force is discontinued the blunt cannula assembly will return to a position wherein the cutting edge of the access cannula is contained within the passageway of the blunt cannula. All relative motions are generally axial and prompted by forces transmitted through the distal end of the blunt cannula.

What is claimed is:

1. A fluid transfer device comprising:

an access cannula assembly including an access cannula having a proximal end, a distal end, and a lumen therethrough, a cutting edge at said distal end of said cannula for piercing a vial stopper or pierceable septum of an injection site, and a hub having an open proximal end and a distal end joined to said proximal end of said access cannula so that said lumen is in fluid communication with said open proximal end of said hub;

a blunt cannula assembly including a blunt cannula having a proximal end, a blunt distal end, and a passageway therethrough, and a housing having an open proximal end and a distal end joined to said proximal end of said blunt cannula, a portion of said access cannula being positioned within said passageway of said blunt cannula;

spring means for helping to position said access cannula within said passageway of said blunt cannula wherein a proximally directed force applied to said blunt cannula will cause said spring to deflect and said cutting edge of said access cannula to project distally outwardly past the distal end of said blunt cannula; and sealing means for sealing said access cannula assembly and said blunt cannula assembly so that pressurized liquid passing distally through said access cannula will exit said fluid transfer device through said distal end of said blunt cannula.

2. The fluid transfer device of claim 1 wherein said sealing means includes an elastomeric element sealing space between said hub and said housing.

3. The fluid transfer device of claim 1 wherein said sealing means includes an elastomeric element sealing space between said access cannula and said housing.

4. The fluid transfer device of claim 1 wherein said sealing means comprises said cannula being large enough to help prevent liquid from passing between the outside of said access cannula and the inside of said passageway of said blunt cannula.

5. The fluid transfer device of claim 1 further including means for connecting said hub and said housing to prevent said blunt cannula assembly from being separated from said access cannula assembly.

6. The fluid transfer device of claim 5 wherein said means for connecting includes an inwardly directed projection on said housing positioned within a recess in said hub.

7. The fluid transfer device of claim 1 wherein said spring means is positioned between said hub and said housing.

8. The fluid transfer device of claim 1 wherein said spring means includes a cylindrically-shaped elastomeric sleeve surrounding said proximal end of said access cannula.

9. The fluid transfer device of claim 1 wherein said spring means is made of elastomeric material selected from the group of natural rubber, synthetic rubber, and thermoplastic elastomer.

10. The fluid transfer device of claim 1 wherein said spring means and said means for sealing include a cylindrically-shaped elastomeric sleeve.

11. The fluid transfer device of claim 1 further including torque transmitting means for allowing a rotational force transmitted to said housing to be transmitted to said hub.

12. The fluid transfer device of claim 11 wherein said torque transmitting means includes a protuberance on said hub positioned within a slot in said housing.

13. The fluid transfer device of claim 1 further including a shield having an open proximal end, a distal end and a sidewall therebetween defining a recess in said shield, said shield being removably connected to said fluid transfer device so that said blunt cannula is contained within said recess.

14. The fluid transfer device of claim 1 wherein said blunt cannula and said housing are integrally formed of thermoplastic material.

15. The fluid transfer device of claim 1 wherein said access cannula is formed of metal.

16. The fluid transfer device of claim 1 further including a syringe barrel having an elongate body defining a chamber for retaining fluid, an open proximal end, a distal end and a tip extending from said distal end having a tip passageway therethrough in fluid communication with said chamber, said tip being positioned within said open proximal end of said hub so that said chamber is in fluid communication with said lumen.

17. The fluid transfer device of claim 16 further including a stopper in fluid-tight engagement inside said barrel, and a rigid elongate plunger rod extending proximally from said stopper through said open proximal end of said barrel.

18. A method for transferring an injectable liquid comprising the steps of:
- (a) providing a syringe including a syringe barrel having an elongate cylindrical body defining a chamber for retaining fluid, an open proximal end, a distal end and a tip extending from said distal end having a tip passageway therethrough in fluid communication with said chamber, a stopper in fluid-tight slidable engagement inside said barrel and an elongate plunger rod extending proximally from said stopper through said open proximal end of said barrel;
- (b) providing a fluid transfer device including an access cannula assembly including an access cannula having a proximal end, a distal end, and a lumen therethrough, a cutting edge at said distal end of said access cannula for piercing a vial stopper, and a hub having an open proximal end and a distal end joined to said proximal end of said access cannula so that said lumen is in fluid communication with said open proximal end of said hub; a blunt cannula assembly including a blunt cannula having a proximal end, a blunt distal end, and a passageway therethrough, and a housing having an open proximal end and a distal end joined to said proximal end of said blunt cannula; spring means for helping to position said access cannula within said passageway of said blunt cannula wherein a proximally directed axial force applied to said blunt cannula will cause said spring to deflect and said cutting edge of said access cannula to project distally outwardly past the distal end of said blunt cannula; and means for sealing said access cannula assembly and said blunt cannula assembly so that pressurized liquid passing distally through said access cannula will exit said fluid transfer device through said distal end of said blunt cannula;
- (c) connecting said syringe filling device to said syringe so that said tip is positioned within said open proximal end of said hub and said chamber is in fluid communication with said lumen of said access cannula;
- (d) providing a vial having a pierceable stopper and containing an injectable liquid;
- (e) placing said blunt distal end of said blunt cannula in contact with said pierceable stopper;
- (f) moving said syringe barrel toward said septum causing said spring to deflect and move said blunt cannula assembly proximally and causing said cutting edge on said distal end of said access cannula to pierce said pierceable stopper to establish fluid communication between the interior of said vial and the chamber of said syringe;
- (g) withdrawing the desired amount of injectable liquid from said vial into said chamber by moving said plunger rod in a proximal direction with respect to said barrel; and
- (h) withdrawing said access cannula from said stopper of said vial.

19. The method of claim 18 further comprising the steps of:
- (i) moving said syringe and fluid transfer device to an I.V. set having an injection site with a pre-slit septum;
- (j) advancing said syringe towards said pre-slit septum so that said blunt tip of said blunt cannula pierces said septum and establishes fluid communication with said I.V. set; and
- (k) advancing said plunger so that said stopper moves said fluid from said chamber through said lumen and into said I.V. set.

20. The method of claim 18 further comprising the steps of:
- (l) moving said syringe and fluid transfer device to an I.V. set having an injection site with a pierceable septum;
- (m) advance said syringe towards said pierceable septum so that said blunt tip of said blunt cannula contacts said pierceable septum;
- (n) moving said syringe barrel toward said pierceable septum causing said spring to deflect and move said blunt cannula assembly proximally and causing said cutting edge on said distal end of said access cannula to pierce said pierceable septum to establish fluid communication with said I.V. set; and
- (o) advancing said plunger so that stopper moves said fluid from said chamber through said lumen and into said I.V. set.

* * * * *